US009757140B2

(12) United States Patent
Hernandez Juanpera (10) Patent No.: US 9,757,140 B2
(45) Date of Patent: Sep. 12, 2017

(54) LAPAROSCOPIC SURGICAL INSTRUMENT

(71) Applicant: SERVOCAD MICROTRONICS, S.L, Barcelona (ES)

(72) Inventor: Jesus Hernandez Juanpera, Barcelona (ES)

(73) Assignee: SERVOCAD MICROTRONICS, S.L, Barcelona (ES)

(*) Notice: Subject to any disclaimer, the term of this patent is extended or adjusted under 35 U.S.C. 154(b) by 373 days.

(21) Appl. No.: 14/396,222

(22) PCT Filed: Mar. 12, 2013

(86) PCT No.: PCT/ES2013/070159
§ 371 (c)(1),
(2) Date: Oct. 22, 2014

(87) PCT Pub. No.: WO2013/160503
PCT Pub. Date: Oct. 31, 2013

(65) Prior Publication Data
US 2015/0112382 A1    Apr. 23, 2015

(30) Foreign Application Priority Data
Apr. 23, 2012    (ES) .................................. 201230596

(51) Int. Cl.
*A61B 17/29*    (2006.01)
*A61B 18/14*    (2006.01)

(52) U.S. Cl.
CPC .......... *A61B 17/29* (2013.01); *A61B 17/2909* (2013.01); *A61B 18/1445* (2013.01);
(Continued)

(58) Field of Classification Search
CPC .... A61B 2017/2938; A61B 2017/2927; A61B 2017/2946; A61B 17/29; A61B 2017/2932; A61B 18/1445
See application file for complete search history.

(56) References Cited

U.S. PATENT DOCUMENTS

| 5,827,323 A | 10/1998 | Klieman et al. |
| 2002/0072766 A1 | 6/2002 | Hunt et al. |
| 2005/0075664 A1 | 4/2005 | Nagase et al. |

FOREIGN PATENT DOCUMENTS

| EP | 0557806 A2 | 9/1993 |
| ES | 2114962 T3 | 6/1998 |

(Continued)

OTHER PUBLICATIONS

International Search Report and Written Opinion dated Jul. 17, 2013; PCT/ES2013/070159.

*Primary Examiner* — Thomas McEvoy
(74) *Attorney, Agent, or Firm* — Ladas & Parry LLP (57) ABSTRACT

The invention relates to a completely mechanical laparoscopic surgical instrument which can be disposed of after a single use or which can be sterilized and re-used more than once. The instrument essentially comprises: a gripping zone provided with two gripping elements (2, 3) hinged to one another by means of a pivot shaft (4), a working tool (30) provided with two jaws hinged to one another by means of a pivot shaft, and an actuation mechanism that can transmit movement from the gripping zone to the working tool (30). According to the invention, the tool can adopt multiple positions and/or orientations during its use with the assistance of substantially annular bodies that are coupled to connecting rods associated with the gripping elements.

20 Claims, 9 Drawing Sheets

(52) U.S. Cl.
CPC . *A61B 2017/291* (2013.01); *A61B 2017/2927* (2013.01); *A61B 2017/2929* (2013.01); *A61B 2017/2938* (2013.01); *A61B 2217/007* (2013.01)

(56) References Cited

FOREIGN PATENT DOCUMENTS

| | | |
|---|---|---|
| ES | 2333509 A1 | 2/2010 |
| ES | 2337984 T3 | 5/2010 |
| ES | 2369530 T3 | 12/2011 |
| WO | 01/66025 A1 | 9/2001 |
| WO | 2011/042584 A1 | 4/2011 |
| WO | 2013/160503 A1 | 10/2013 |

LAPAROSCOPIC SURGICAL INSTRUMENT

OBJECT OF THE INVENTION

The purpose of the invention patent application herein is to register a laparoscopic surgical instrument that incorporates significant innovations and advantages.

More specifically, the invention proposes the development of a completely mechanically-operated laparoscopic surgical instrument, which can be disposed of after a single use or which can be sterilised and reused more than once, which can be very useful for laparoscopy and endoscopic procedures due to the fact that the working tool can adopt multiple positions and/or orientations when being used.

BACKGROUND OF THE INVENTION

At present laparoscopic surgical devices intended for surgical operations that require suturing and ligating of body tissues by means of incisions made in the walls of the body are well known. However, in a large majority of these devices, the surgical tool (two jaws hinged together) acts in a single plane, hence offering a very limited degree of freedom that makes it difficult for the surgeon to use, although the shaft or tube connecting the gripping zone with the jaw members can be rotated on some of them.

To resolve the aforementioned problem, a laparoscopic instrument that is described in European patent EP-A-1 250891 is known. This instrument is known for comprising a pair of coupling mechanisms that can link, on the one hand, a gripping element to a jaw member while the second gripping element is linked to the second jaw member. Additionally, the two gripping elements can rotate relative to the second plane due to the structural configuration of the two attachment mechanisms.

However, this instrument is relatively complex and its freedom of movement remains limited as a 360° rotation of the axis that connects the jaw members with the gripping elements is not possible, and handling this instrument during surgery still involves some difficulty.

DESCRIPTION OF THE INVENTION

The invention herein has been developed with the aim of providing a laparoscopic surgical instrument that is considered a novelty within the field of application and resolves the aforementioned drawbacks, further providing other additional advantages that will be apparent from the description detailed hereinafter.

It is therefore an object of this invention to provide a laparoscopic surgical instrument which primarily includes a gripping zone provided with two gripping elements hinged to one another by means of a pivot shaft; a working tool provided with two gripping elements hinged to one another by means of a pivot shaft; and an actuation mechanism that can transmit movement from the gripping zone to the working tool.

In particular, the invention is characterised in that said actuation mechanism comprises two push rods, wherein the distal end of each of the push rods is connected to a respective jaw and the proximal end is pivotally connected to a respective substantially annular body, the two substantially annular bodies being able to move longitudinally, such that the push rods can fully rotate relative to the central axis of the substantially annular body. The two substantially annular bodies are arranged slidably in a swinging movement on an elongated tubular portion through which the two push rods run along, in which each gripping element is coupled to two substantially annular bodies by two connecting rods, each one of said connecting rods being pivotally joined to a substantially annular body.

The central axis of the pivot shaft on which both gripping elements are hinged, the central shafts corresponding to the attachment points of the ends of the connecting rods that are attached to such gripping elements are aligned with each other in all operating conditions, therefore the two gripping elements can act together and/or independently of each other for joint and/or separate actions on one or both jaws.

Thanks to these characteristics, a completely mechanically-operated instrument is obtained, namely, free from electronic components, which provides a degree of freedom of movement for the jaw members compared to currently known laparoscopy instruments since it not only allows independent movement of each of the two jaws in different inclined positions relative to the longitudinal axis of the instrument but also allows a 360 degree rotation in a simple and intuitive way for the surgeon.

With no electronic components required for operation, the manufacturing costs are reduced and therefore it can be disposable. In addition, another advantageous aspect is the fact that the use of components that are sensitive to moisture or electromagnetic radiation that require, for example, additional sealing elements is prevented.

It will be apparent to one skilled in the art that the jaw members that form, for example, a clip can be substituted by cutters, pincers or scalpels which can also be disposed of after use.

According to another aspect of the invention, each push rod has an end extending perpendicularly relative to the rest of the body of the push rod that is rotably coupled in a groove which runs in a guided manner along the inner wall of the substantially annular body.

Advantageously, the connecting rods have a central portion serving as a rod that can be adjusted in length.

Preferably, guiding means are provided for the linear displacement of the ends of the connecting rods attached to the substantially annular bodies. In a preferred embodiment, the guide means comprise a plate provided with two windows through which extensions of the substantially annular bodies protrude in which screws are set which fix the connecting rod to the substantially annular body, such that the extensions move linearly through such windows.

Each gripping element includes a number of retaining means at the upper part thereof. Said retaining means have a fixed part on the upper part of the gripping element which includes an extension in the form of a toothed sector and a fixed protrusion located on said extension in the form of a toothed sector such that it meshes with the toothed sector. Furthermore, the retaining means may include a fastener that locks the extension in the form of a toothed sector in position.

The fastener comprises a linearly displaceable rod section that has a protrusion at its lower part that can be fitted into a groove that is part of a plurality of grooves below the toothed area.

Preferably, the instrument comprises return means for returning one or both gripping elements to a predetermined position after an angular displacement of at least one of the gripping elements.

Additionally, it also has blocking means for blocking the movement of one of the gripping elements relative to the other gripping element. Said blocking means have a manually operable trigger located in one of the gripping elements that acts on a ratchet fixed to the other gripping element.

Advantageously, it is provided with at least one connection socket for connecting to a source of electrical power supply, such that it transmits an electrical voltage to the working tool. Additionally, two connection sockets may be provided.

Also advantageously, one of the gripping elements includes an extension having a curved trajectory, in particular the gripping element located the closest to the working tool during a condition of use, such that it makes it easier for the surgeon to grip the instrument when handling the latter.

Preferably, provision has been made for the arrangement of a protective housing that at least partially surrounds the actuation mechanism, such that it is protected from dirt and any knocks.

According to another object of the invention, a third push rod is provided that runs parallel with respect to the two push rods mentioned above which is fixed at one end to a hinge connected to the working tool, such that the working tool can move to the right and/or left relative to the position of said push rod.

According to another characteristic, one part of the push rods are housed in a number of grooves present in a guide support, such that they are protected from the outside by preventing them from becoming bent or damaged, said push rods being guided properly and reliably.

Other characteristics and advantages of the laparoscopic surgical instrument object of the invention herein will become apparent from the description of a preferred, although not exclusive embodiment, which is illustrated by way of non-limiting example in the drawings appended, in which:

DESCRIPTION OF A PREFERRED EMBODIMENT

In view of the mentioned figures and according to the adopted numbering, an example of a preferred embodiment of the invention can be seen therein, which comprises the parts and elements indicated and described in detail below.

Thus, as shown in the accompanying figures, a laparoscopic surgical instrument, indicated generally by the reference (1), comprises a gripping zone provided with two gripping elements (2, 3) hinged together by a pivot shaft (4), a working tool (30) provided with two jaws (31, 32) hinged together by a pivot shaft (33) and an actuation mechanism that can transmit movement from the gripping zone to the working tool (30), said actuation mechanism being described in greater detail below.

Figure 1:
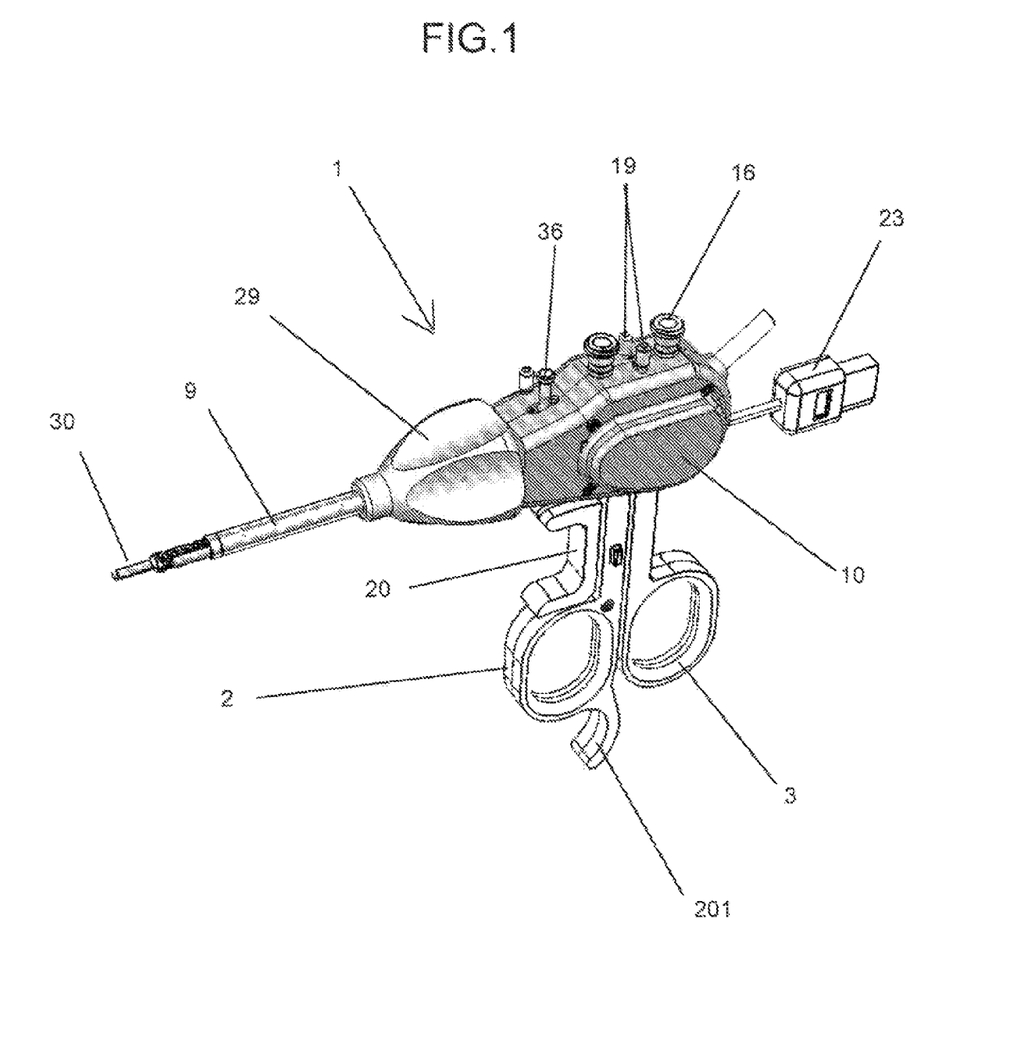
FIG. 1.—Perspective view of a laparoscopic surgical instrument according to the invention herein with the working tool in a closed position.
Figure 2:
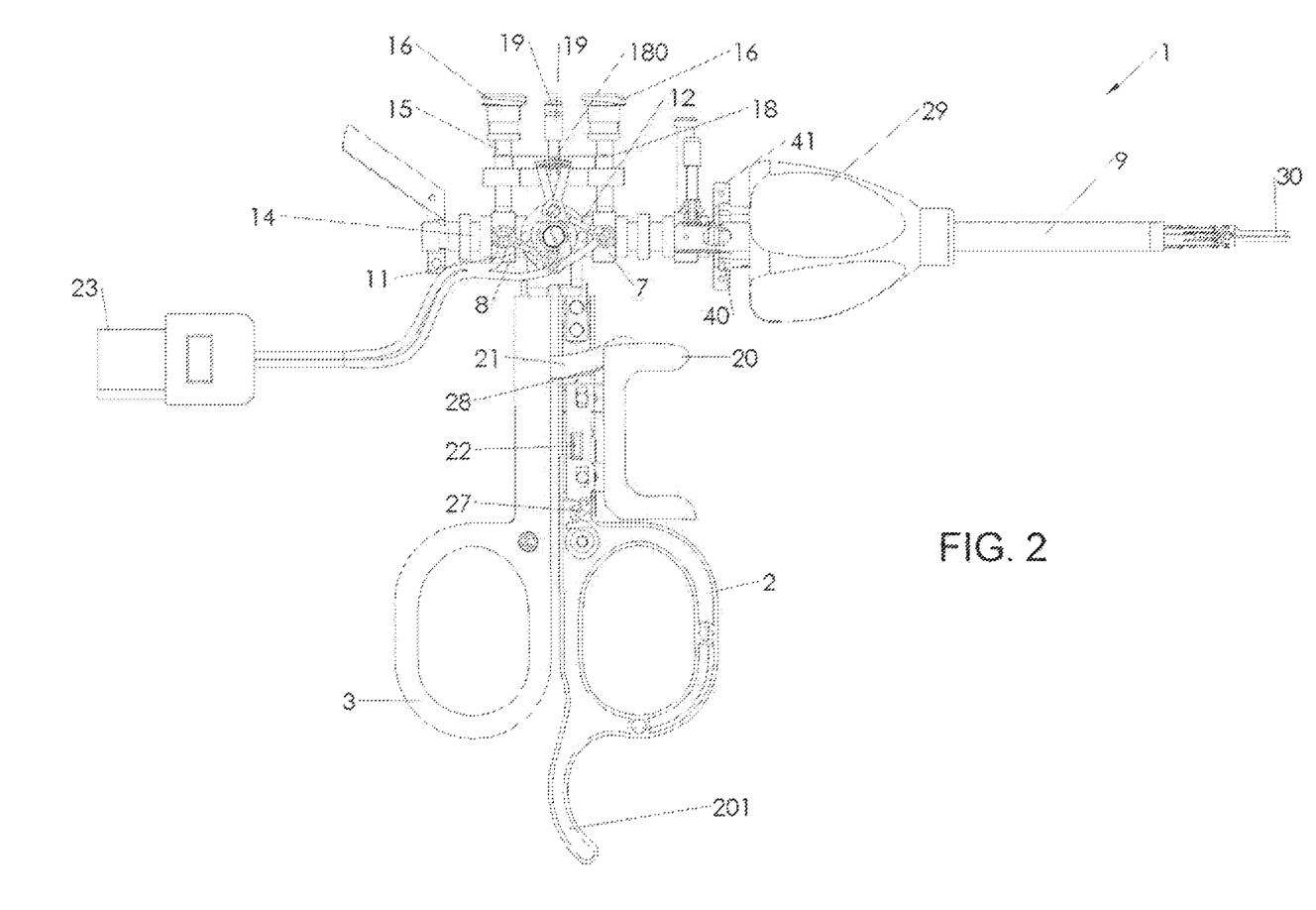
FIG. 2.—Schematic side elevated view of the laparoscopic surgical instrument with the jaw members in a closed position and in which the main parts of the actuation mechanism are shown.

The two gripping elements (2, 3) have an elongated shape with a thimble, which are very similar in form to conventional scissors thimbles. The gripping element (2) has an extension having a curved trajectory (201) on a lower part thereof, as shown in FIGS. 1 and 2.

Now, with particular reference to the aforementioned actuation mechanism, it comprises two elongated push rods (5, 6) with a square cross-section and made of a metal or electrically-conductive material that run parallel to each other, wherein the distal end of each of the push rods (5, 6) is hingedly connected to a respective jaw (31, 32) and the proximal end is pivotally connected to a respective substantially annular body (7, 8).

Figure 10:
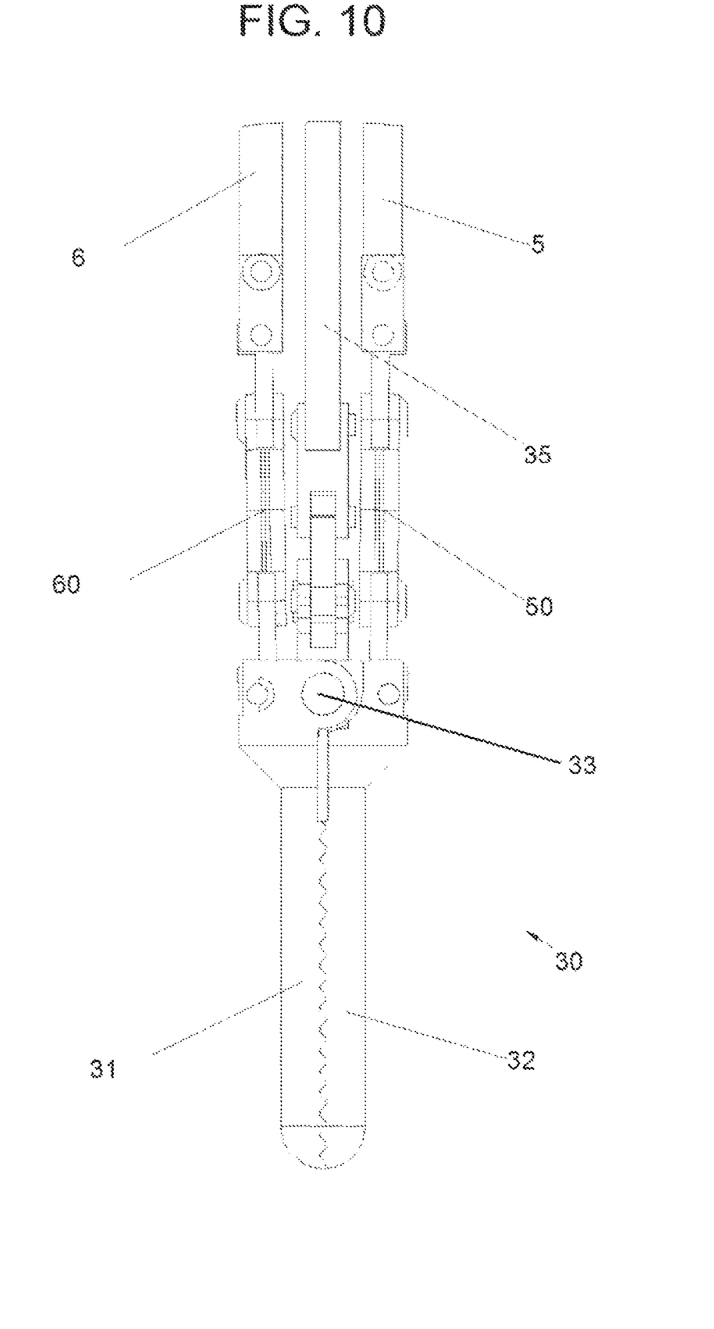
FIG. 10.—Detailed top-down plan view of the area where the jaw members are.
Figure 11:
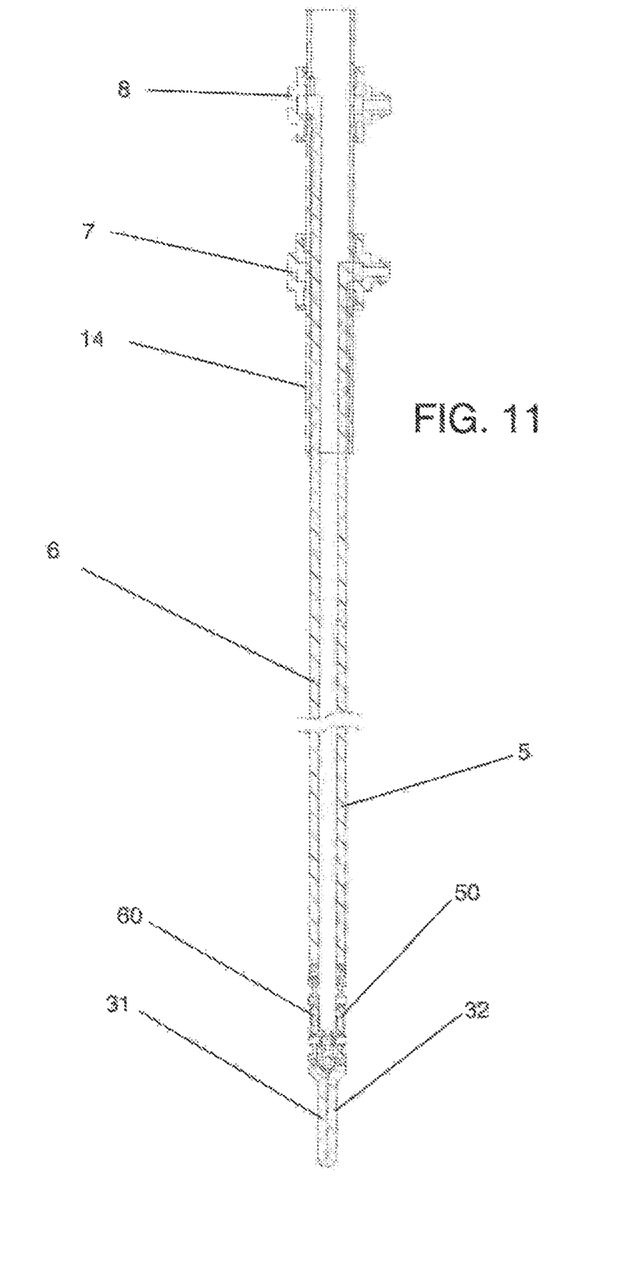
FIG. 11.—Schematic plan view in which the arrangement of the push rods is shown relative to the substantially annular bodies.

The connection between the push rods (5, 6) and the corresponding jaws (31, 32) is made by means of intermediate joints (50, 60), respectively, as seen more clearly in FIGS. 10 and 11.

The two substantially annular bodies (7, 8) can further move longitudinally, allowing the tubular portion (14) to rotate on its own axis, such that the push rods (5, 6) can be rotated completely relative to the central axis of the substantially annular body, namely, up to 360°, thereby changing the position or orientation of the working tool, without ceasing to actuate or move due to the action of one or both gripping elements (2, 3). In order to activate the rotation action, a rotating wheel (29) is used that can rotate manually in both directions, such that it allows the working tools to rotate on their axis regardless of the position of the gripping element (2, 3).

An insulating cover (9) is provided around one part of the two push rods (5, 6) which is outside a protective housing (10) that protects the actuation mechanism.

This protective housing (10) is formed by two halves that can be joined together, for example, from plastic material, provided with multiple holes through which the parts necessary for proper operation of the surgical instrument (1) protrude. For clarity, this protective housing (10) is only shown in FIG. 1.

These two substantially annular bodies (7, 8) are arranged slidably in a swinging movement on an elongated tubular portion (14) through which the two push rods (5, 6) run along, in which each gripping element (2, 3) is coupled to the two substantially annular bodies (7, 8) by means of a set of two connecting rods (11, 12). Said elongated tubular portion (14) is connected to the rotating wheel (29) such that it enables the rotation of the push rods (5, 6).

The rotating wheel (29) is coupled to a pinion (40) that is in contact with an elastic plate (41) secured through a protuberance that acts as retaining means in order to prevent the idle rotation of the rotating wheel (29).

Figure 8:
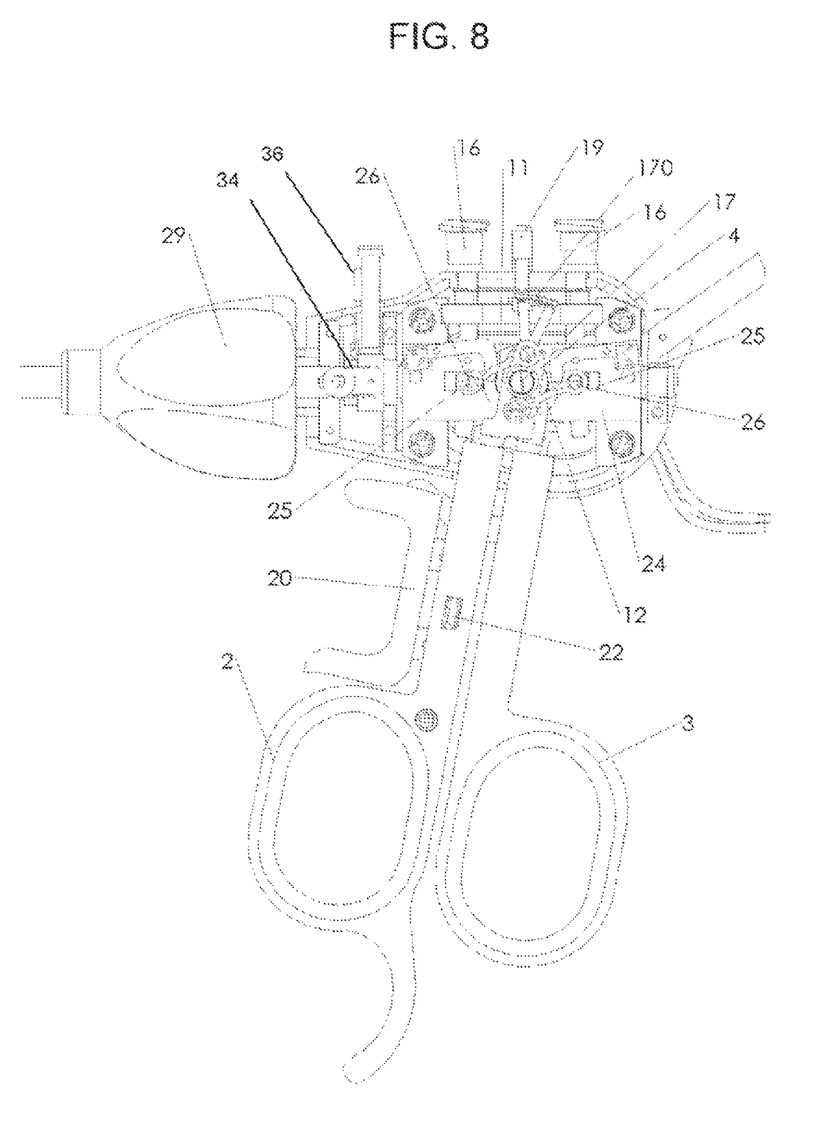
FIG. 8.—Detailed view of the actuation mechanism when the working tool is in the position shown in FIG. 4.

As seen in FIG. 8, each of said connecting rods (11, 12) is pivotally attached to a substantially annular body by means of bolting elements (26) located at each end of the connecting rods. Each set of connecting rods (11, 12) is located on each side of the surgical instrument (1) relative to its longitudinal central axis.

Figure 12:
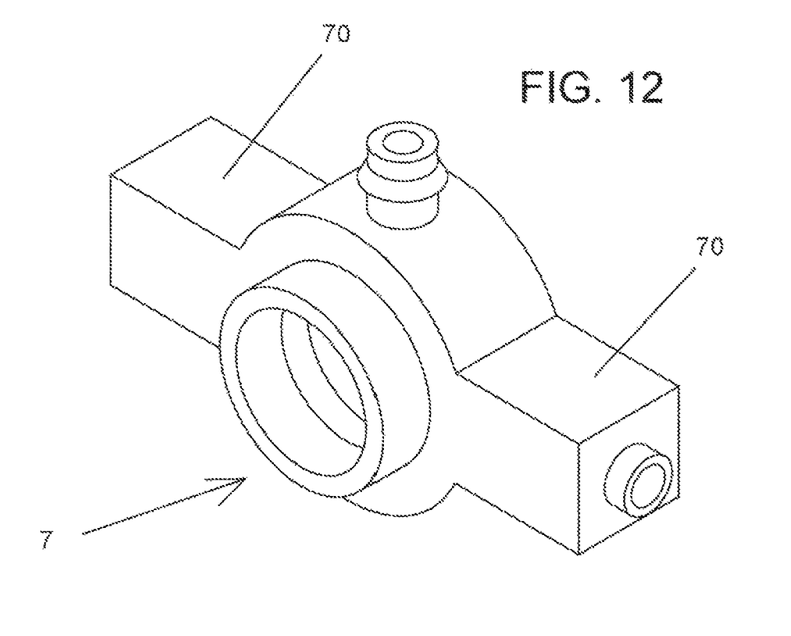
FIG. 12.—Detailed perspective view of a substantially annular body.
Figure 13:
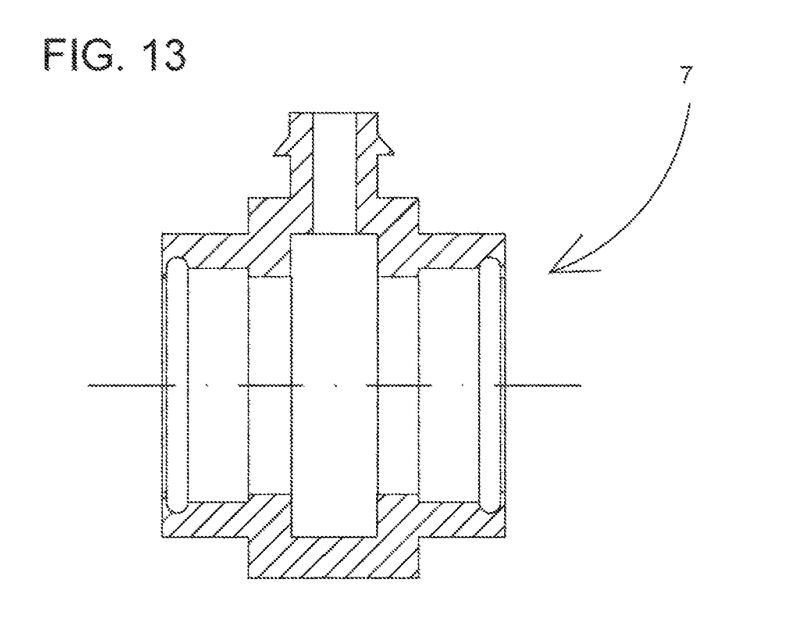
FIG. 13.—Detailed cross-sectional view of the ring shown in the previous figure.

Such bolting elements (26) are fixed in through-holes located on two protrusions (70) that protrude outwardly and which are diametrically opposite, as seen in detail in FIGS. 12 and 13.

It is worth noting that the central shafts corresponding to the attachment points of the ends of the connecting rods (11, 12) that are attached to such gripping elements are aligned with each other in all operating conditions, therefore the two gripping elements can act together and/or independently of each other for joint and/or separate actions on one or both jaws.

Each push rod (5, 6) has a end (50, 60) extending perpendicularly relative to the rest of the body of the push rod (5, 6) that is rotably coupled in a groove which runs in a guided manner along the inner wall of the substantially annular body (7, 8).

To ensure the linear displacement of the ends of the connecting rods attached to the substantially annular bodies, a plate (24) provided with two windows (25) is provided through which extensions of the substantially annular bodies protrude in which screws are set (26) which fix the connecting rod to the substantially annular body, such that the extensions move linearly through such windows (25). It is understood that the instrument herein (1) is provided with two identical plates, a plate (24) for each set of two connecting rods (11, 12).

Finally, a third push rod (35) is provided that runs parallel relative to the two push rods which is secured at one end to a hinge attached to the working tool (30) to rotate said working tool (30) to the right and/or left with respect to the longitudinal axis of said third push rod (35). This movement is performed by moving the part of the instrument that protrudes from the housing forwards or backwards by means of a zip system (34) which is connected to said third push rod (35) and a lever (36) that protrudes vertically, said zip system (34) being located inside the protective housing (10). To prevent the inadvertent movement of the third push rod (35), blocking means that act on the zip system (34) have been included to prevent its displacement.

Figure 3:
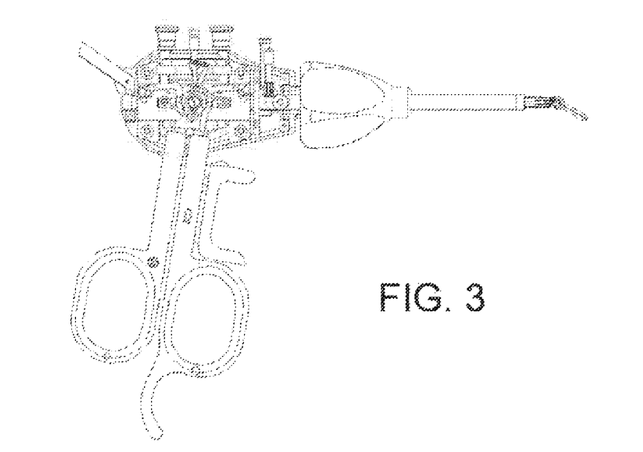
FIG. 3.—Side elevation view of the laparoscopic surgical instrument in which the jaw members are closed to each other and in a downwardly inclined position.
Figure 4:
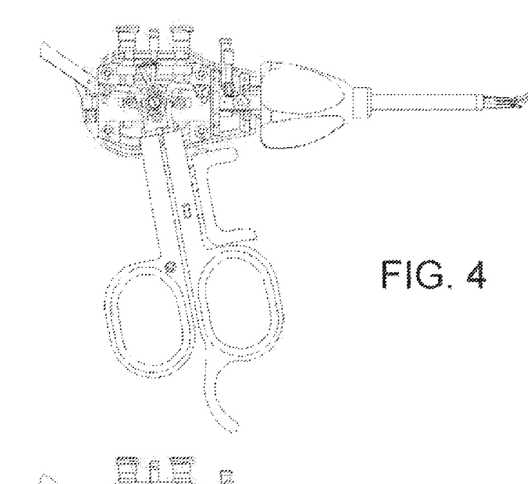
FIG. 4.—Side elevation view of the laparoscopic surgical instrument in which the jaw members are closed to each other and in an upwardly inclined position.
Figure 5:
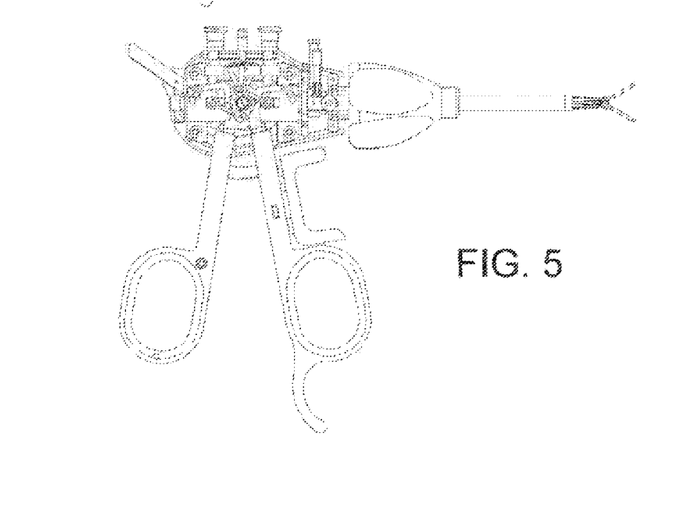
FIG. 5.—Side elevation view of the laparoscopic surgical instrument in which the jaw members are open.
Figure 6:
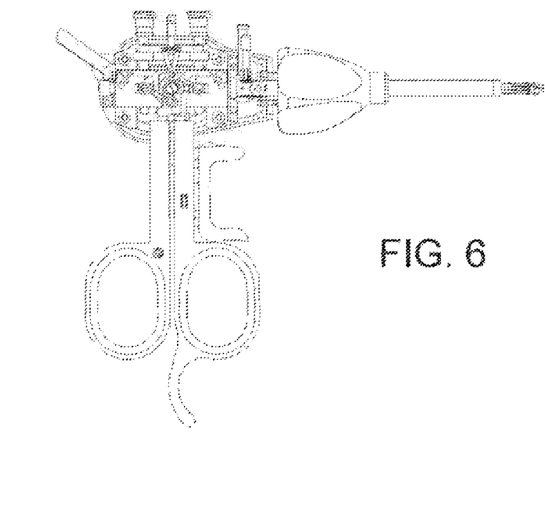
FIG. 6.—Side elevation view of the laparoscopic surgical instrument in which the jaw members are closed.
Figure 7:
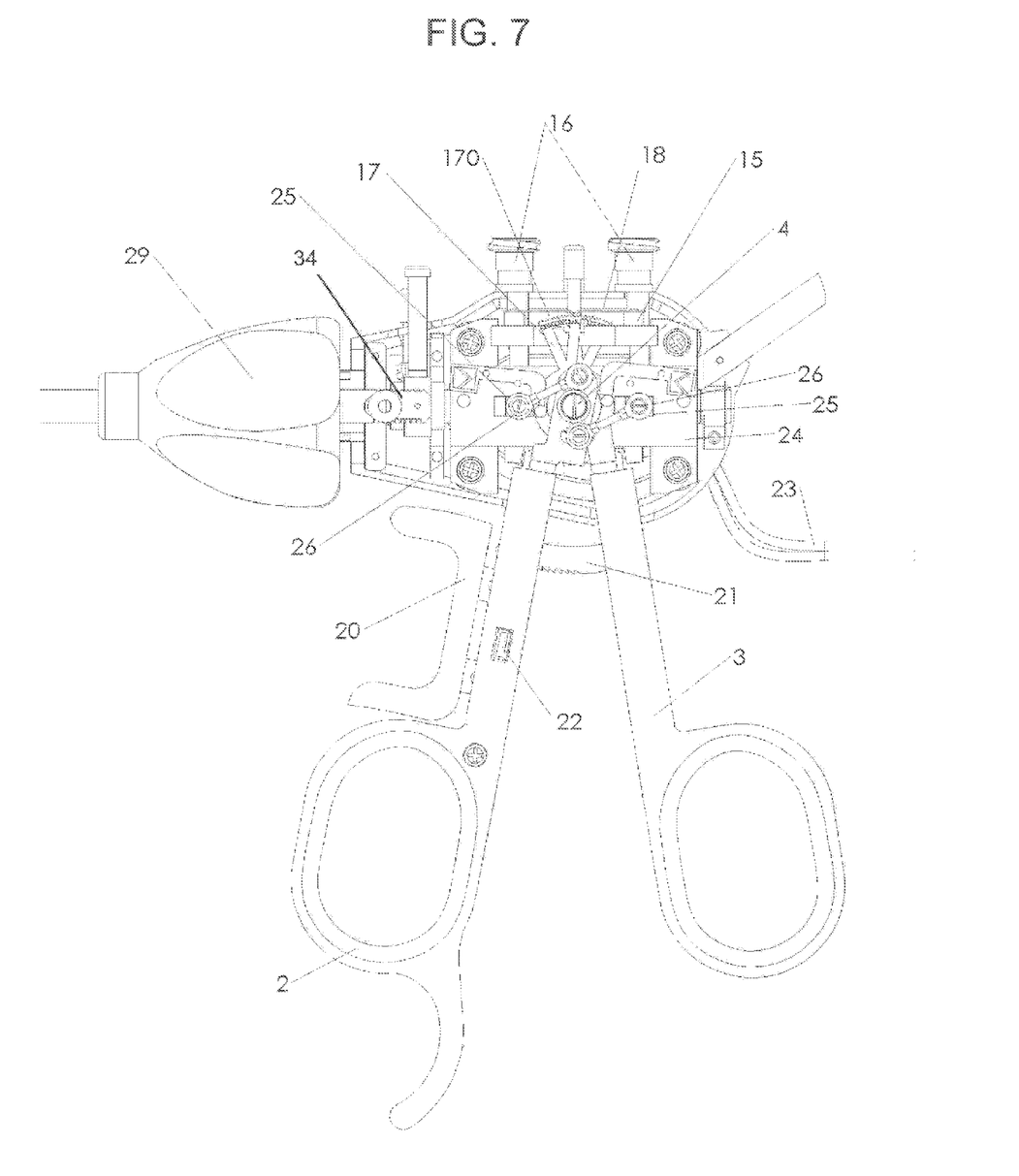
FIG. 7.—Detailed view of the transmission mechanism when the working tool is open, as shown in FIG. 5.
Figure 9:
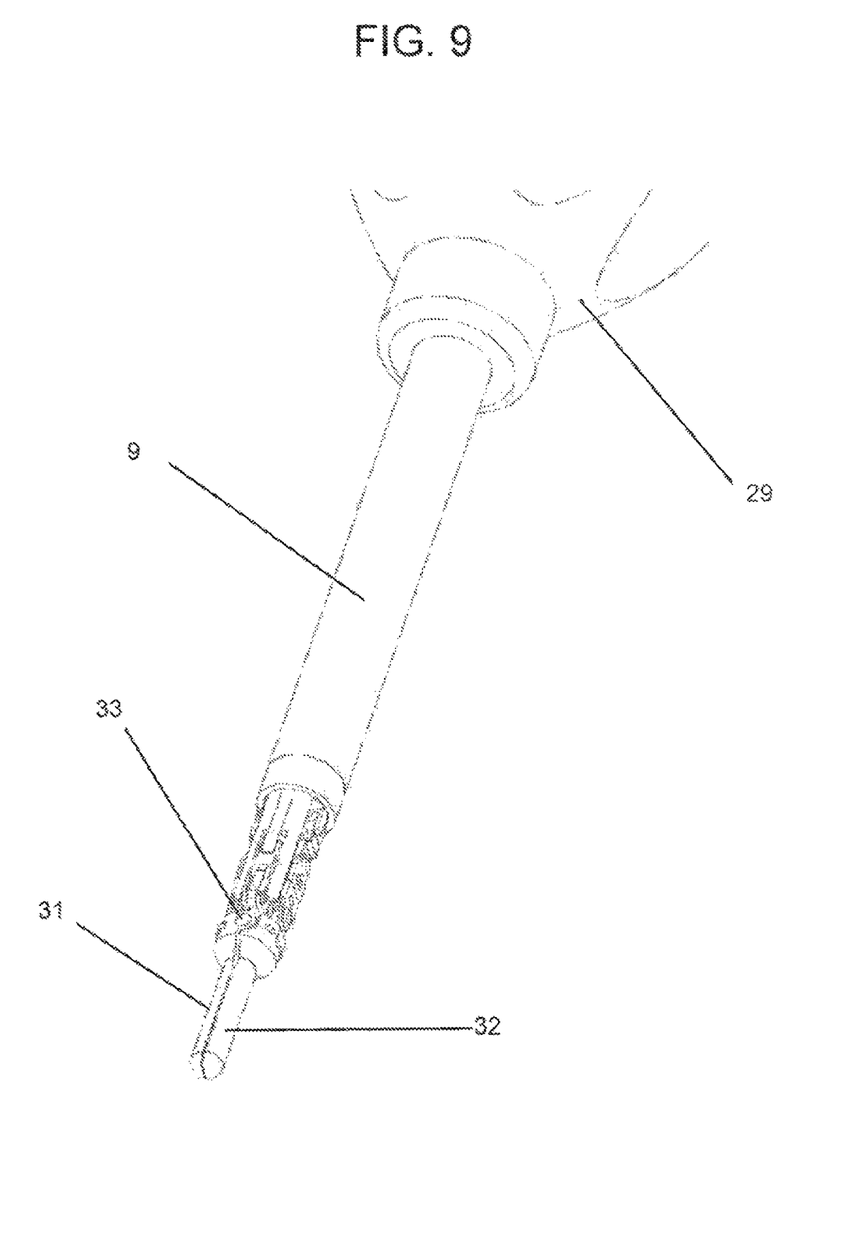
FIG. 9.—Detailed perspective view of the area where the jaw members are hinged.

This actuation mechanism described above advantageously allows the working tool to adopt multiple positions, namely, the two jaws can be oriented either in an open or closed position, upwards, downwards, to the right or to the left, as shown in some examples of positioning of the working tool in FIGS. 3, 6 and 9. Such positions are conducted by the movement, simultaneously or individually, towards and away from a gripping element (2, 3) relative to another gripping element (3, 2), the joint swivel movement of both gripping elements (2, 3) relative to the longitudinal axis defined by the push rods and the rotation of the rotating wheel (29).

Each gripping element (2, 3) includes retaining means at the upper part thereof having a fixed part (17) on the top of the gripping element that includes an extension (170) in the form of a toothed sector and a protrusion (180) formed in a centred manner on a laminar plate (18) which is fixed and located on said extension (170) in the form of a toothed sector such that it meshes with the toothed sector. Furthermore, the retaining means include a fastener (19) that locks the extension (170) in the form of a toothed sector in position. It should be mentioned that two fasteners (19) are provided; one associated with each fixed part (17).

The surgical instrument (1) also has blocking means for blocking the movement of one of the gripping elements relative to the other gripping element. When a part of the gripping element (2) is removed, these blocking means, which can be seen in detail in FIG. 2, have a trigger (20) with a substantially C shape which is operable manually using elastic return means (27) arranged downwardly, the trigger (20) being located in the gripping element (2) which acts by means of a protrusion (28) on a ratchet (21) attached to the other gripping element (3). The actuation of the ratchet (21) can be cancelled voluntarily by means of a switch (22) which is easily accessible and located on the gripping element (2).

A connection socket (23) is provided at the rear of the surgical instrument (1), for example, the bipolar type for connecting to a source of electrical power supply; therefore a voltage can be transmitted to the working tool, if necessary. It will be apparent that more than one connection socket can be included in the surgical instrument (1) described herein.

Finally, a pair of inlet sockets (16) are provided at the top in order to connect a conduit for supplying a fluid that can be used for medical purposes, if it were required.

The details, shapes and dimensions and other accessory elements as well as the materials used in the manufacture of the laparoscopic surgical instrument of the invention may be conveniently replaced by others which are technically equivalent and do not depart from the essential nature of the invention or from the scope defined by the claims provided hereinafter.

The invention claimed is:
1. Laparoscopic surgical instrument comprising:
  a gripping zone provided with two gripping elements hinged to one another by means of a pivot shaft;
  a working tool provided with two jaws hinged to one another by means of a secondary pivot shaft;
  an actuation mechanism that can transmit movement from the gripping zone to the working tool,
  wherein said actuation mechanism comprises:
  two push rods, wherein the distal end of each of the push rods is hingedly connected to a respective jaw and the proximal end is pivotally connected to a respective substantially annular body, the two substantially annular bodies being able to move longitudinally, such that the push rods can fully rotate about the central axis of the substantially annular body by means of linked rotating means;
  the two substantially annular bodies being arranged slidably in a swinging movement on an elongated tubular portion through which the two push rods run along, said tubular portion being associated with said rotation means,
  in which each gripping element is coupled to the two substantially annular bodies by means of two connecting rods, each one of said connecting rods pivotally joined to one of the substantially annular bodies, and
  in which central shafts corresponding to the attachment points of the ends of the connecting rods that are attached to such gripping elements are aligned with each other in an operating condition, such that the two gripping elements are configured for acting together and/or independently of each other for joint and/or separate actions on one or both jaws.

2. Laparoscopic surgical instrument according to claim 1, wherein each push rod has an ending that extends perpendicularly relative to the body of the push rod that is ratably coupled in a groove that runs in a guided manner along a inner wall of the substantially annular body.

3. Laparoscopic surgical instrument according to claim 1, wherein the connecting rods have a central portion serving as a rod that can be adjusted in length.

4. Laparoscopic surgical instrument according to claim 1, wherein guide means are provided for the linear displacement of the ends of the connecting rods attached to the substantially annular bodies.

5. Laparoscopic surgical instrument according to claim 4, wherein the guide means comprise a plate provided with two windows through which extensions of the substantially annular bodies protrude in which screws are set which fix the respective connecting rod to the respective substantially annular body, such that the extensions move linearly through such windows.

6. Laparoscopic surgical instrument according to claim 1, wherein each gripping element includes a number of retaining means at the upper part thereof.

7. Laparoscopic surgical instrument according to claim 6, wherein said retaining means have a part fixed on the upper part of the gripping element, said part comprising an extension in the form of a toothed sector and a fixed protrusion located on said extension in the form of a toothed sector such that it meshes with the toothed sector.

8. Laparoscopic surgical instrument according to claim 6, wherein the retaining means includes a fastener that locks the extension in the form of a toothed sector in position.

9. Laparoscopic surgical instrument according to claim 8, wherein the fastener comprises a linearly displaceable rod section that has a protrusion at its lower part that can be fitted into a groove that is part of a plurality of grooves below the toothed area.

10. Laparoscopic surgical instrument according to claim 1, wherein the instrument comprises return means for returning one or both gripping elements to a predetermined position after an angular displacement of at least one of the gripping elements.

11. Laparoscopic surgical instrument according to claim 1, wherein the instrument has blocking means for blocking the movement of one of the gripping elements relative to the other gripping element.

12. Laparoscopic surgical instrument according to claim 11, wherein said blocking means have a manually operable trigger located in one of the gripping elements which actuates on a ratchet fixed in the other gripping element.

13. Laparoscopic surgical instrument according to claim 1, wherein the instrument has at least one connection socket for connecting to a source of electrical power supply such that it transmits a voltage to the working tool.

14. Laparoscopic surgical instrument according to claim 1, wherein one of the gripping elements includes an extension having a curved trajectory on the lower part thereof, in particular arranged on the gripping element located closer to the working tool during a condition of use.

15. Laparoscopic surgical instrument according to claim 1, wherein the instrument includes a protective housing that at least partially surrounds the actuation mechanism.

16. Laparoscopic surgical instrument according to claim 1, wherein the push rods have a square or rectangular cross-section.

17. Laparoscopic surgical instrument according to claim 1, wherein the substantially annular body includes two protrusions that protrude outwardly and which are diametrically opposite provided with through-holes.

18. Laparoscopic surgical instrument according to claim 1, wherein rotation means comprise a rotary wheel that is linked to the elongated tubular portion.

19. Laparoscopic surgical instrument according to claim 1, wherein a third push rod is provided which runs parallel relative to the two push rods which is secured at one end to a hinge attached to the working tool to rotate the working tool to the right and/or left with respect to the longitudinal axis of said push rod, said third push rod being connected to a zip system provided with blocking means to activate/prevent actuation of said zip system.

20. Laparoscopic surgical instrument according to claim 19, characterised by the fact that it includes actuation means for moving the zip system which have a lever projecting outwardly from the inside of the protective housing.

* * * * *